United States Patent
Shah

(10) Patent No.: US 7,578,809 B2
(45) Date of Patent: Aug. 25, 2009

(54) SURFACE MODIFIED VISCOELASTICS FOR OCULAR SURGERY

(75) Inventor: Mandar V. Shah, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 29 days.

(21) Appl. No.: 11/294,247

(22) Filed: Dec. 5, 2005

(65) Prior Publication Data

US 2006/0090766 A1  May 4, 2006

Related U.S. Application Data

(62) Division of application No. 10/380,135, filed as application No. PCT/US02/41247 on Dec. 20, 2002, now abandoned.

(60) Provisional application No. 60/342,916, filed on Dec. 21, 2001.

(51) Int. Cl.
*A61F 9/007* (2006.01)
(52) U.S. Cl. .................................... 604/290
(58) Field of Classification Search ....................... None
See application file for complete search history.

(56) References Cited

U.S. PATENT DOCUMENTS

| | | | |
|---|---|---|---|
| 4,328,803 A | 5/1982 | Pape | |
| 4,443,432 A | 4/1984 | Garabedian et al. | |
| 4,983,585 A | 1/1991 | Pennell et al. | |
| 5,273,056 A | 12/1993 | McLaughlin et al. | |
| 5,409,904 A | 4/1995 | Hecht et al. | |
| 5,498,606 A | 3/1996 | Harrison et al. | |
| 5,627,162 A | 5/1997 | Gwon et al. | |
| 5,792,103 A | 8/1998 | Schwartz et al. | |
| 6,632,423 B2 | 10/2003 | Doshi et al. | |
| 6,906,044 B2 | 6/2005 | Hermida Ochoa | |
| 7,011,666 B2 * | 3/2006 | Feinsod ..................... | 606/107 |
| 2004/0118414 A1 | 6/2004 | Shah | |

FOREIGN PATENT DOCUMENTS

| | | |
|---|---|---|
| EP | 0 136 782 | 4/1985 |
| JP | 2002-255829 A | 9/2002 |

OTHER PUBLICATIONS

Fernandez-Vigo, J. et al "Elimination of hydroxypropyl methylcellulose from the anterior chamber of the rabbit" J. Cataract Refract. Surg. (1989) vol. 15, No. 2, pp. 191-195.*

Linebarger, E. et al. "Phacoemulsification and modern cataract surgery" Surv. Ophthalmol. (1999) vol. 44, No. 2, pp. 123-147.*

Holzer, M. et al "Effect of Healon5 and 4 other viscoelastic substances . . . " J. Cataract Refract. Surg. (2001) vol. 27, pp. 213-218.*

Berson et al., "Obstruction of Aqueous Outflow by Sodium Hyaluronate in Enucleated Human Eyes, Am. J. Ophthalmology," 95:668 (1983).

Fry, "Postoperative intraocular pressure rises: A comparison of Healon, Amvis, and Viscoat, J. Cataract Refractive Surgery," 15:415 (1989).

Miyauchi eet al., The Optimal Molecular Weight of Dispersive Type Sodium Hyaluronate for the Reduction of Corneal Endothelial Damage Induced by Sonication, Irrigation, and As.

Obstbaum, "Postoperative pressure evaluation. A rational approach to its prevention and management," J. Cataract Refractive Surgery, 18:1 (1992).

Olivius et al., "Intraocular pressure after cataract surgery with Healon®," Am. Intraocular Implant Soc. J., 11:480 (1985).

Silver et al., "Physical Properties of Hyaluronic Acid and Hydroxypropylmethylcellulose in Solution: Evaluation of Coating Ability," J. Applied Biomaterials, 5:89-98 (1994).

Arshinoff, S., Using the dispersive-cohesive viscoelastic soft-shell technique with different ophthalmic viscosurgical devices, Ophthalmic Practice, vol. 18(5):224-226 (2000).

Arshinoff, S., "The Ultimate Soft-shell Technique," Ophthalmic Practice, vol. 18 (6):289-290, 2000.

Miyauchi eet al., The Optimal Molecular Weight of Dispersive Type Sodium Hyaluronate for the Reduction of Corneal Endothelial Damage Induced by Sonication, Irrigation, and As . . . J. Jap. Ophth. (2000) vol. 45 pp. 339-347.

Rainer, G., et al., "Intraocular Pressure Rise After Small Incision Cataract Surgery: A Randomized Intraindividual Comparison Of Two Dispersive Viscoelastic Agents." The British Journal of Opthalmology, England. Feb. 2001. vol. 85(2):139-142.

Holzer, M.P., et al., "Efect of Healon5 and 4 Other Viscoelastic Substances on Intraocular Pressure and Endothelium After Cataract Surgery." Journal of Cataract and Refractive Surgery, United States, Feb. 2001, vol. 27(2):213-218.

* cited by examiner

*Primary Examiner*—Leigh C Maier
(74) *Attorney, Agent, or Firm*—Mark E. Flanigan; Barry L. Copeland

(57) ABSTRACT

Disclosed are surface modified viscoelastics and methods of performing viscosurgery using polymer-containing irrigating solution to reduce cohesiveness of the viscoelastic agent at the interface, thereby improving its performance by reducing the occurrence of unintentional aspiration, especially in ocular surgery.

10 Claims, No Drawings

SURFACE MODIFIED VISCOELASTICS FOR OCULAR SURGERY

CROSS-REFERENCE TO RELATED APPLICATION

This application is a divisional of application Ser. No. 10/380,135 filed Mar. 11, 2003 now abandoned, which itself claims priority from and incorporates by reference commonly owned PCT application Serial No. PCT/US02/41247, filed Dec. 20, 2002, and provisional application Ser. No. 60/342,916, filed Dec. 21, 2001.

FIELD OF THE INVENTION

The present invention relates to the field of surgery utilizing viscous and/or viscoelastic materials, also known as viscosurgery. In particular, the invention involves inclusion of polymeric materials in irrigating solutions to enhance the performance of the viscosurgical materials by altering the rheologies thereof. The invention also relates to methods of using such modified irrigating solutions in conjunction with such viscous or viscoelastic materials in surgical procedures, especially ophthalmic surgical procedures.

BACKGROUND OF THE INVENTION

Viscous or viscoelastic agents used in surgery may perform a number of different functions, including without limitation maintenance and support of soft tissue, tissue manipulation, lubrication, tissue protection, and adhesion prevention. It is recognized that the differing rheological properties of these agents will necessarily impact their ability to perform these functions, and, as a result, their suitability for certain surgical procedures. See, for example, U.S. Pat. No. 5,273,056, the contents of which are by this reference incorporated herein.

Cataracts are opacities of the natural ocular lens which generally arise in the elderly. In order to improve eyesight, the cataractous lens is surgically removed from the eye and an artificial intraocular lens is inserted in its place. During these surgical procedures, viscoelastic materials are typically injected into the anterior chamber of the eye to prevent collapse of the anterior chamber and to protect the delicate eye tissues from damage resulting from physical manipulation.

A number of viscous or viscoelastic agents (hereinafter "agents" or "viscoelastics") are known for ophthalmic surgical use: Viscoat® (Alcon Laboratories, Inc.) which contains sodium hyaluronate and chondroitin sulfate; Provisc® (Alcon), Healon®, Healon® GV, and Healon®5 (Pharmacia Corporation), Amvisc® and Amvisc® Plus (Bausch & Lomb, Inc.), and Vitrax® (Allergan Inc.) all of which contain sodium hyaluronate (hyaluronic acid and its pharmaceutically acceptable salts, such as sodium hyaluronate, are some times hereinafter referred to as HA); and Cellugel® (Alcon) which contains hydroxypropylmethylcellulose (HPMC). All of the foregoing examples of viscoelastics may be used in cataract surgery. They are used by the skilled ophthalmic surgeon for several purposes, including maintenance of the anterior chamber of the eye and protection of ophthalmic tissues during surgery, particularly corneal endothelial cells, and as an aid in manipulating ophthalmic tissues.

While all of the agents described above may be used during cataract surgery, each has certain recognized advantages and disadvantages. Viscoelastics that are dispersive tend to offer better coating and protection of delicate tissues, such as the endothelial lining of the cornea. Cohesive viscoelastics, on the other hand, tend to be "stiffer" offering an advantage in soft tissue manipulation, e.g., capsulorhexis, but do not coat as well and are prone to accidental or premature aspiration. See, Miyauchi et al., "The Optimal Molecular Weight of Dispersive Type Sodium Hyaluronate for the Reduction of Corneal Endothelial Damage Induced by Sonication, Irrigation, and Aspiration," *Jpn J. Ophthalmol.*, 45:339-347 (2001). Thus, during phacoemulsification, a less cohesive, i.e. more dispersive, viscoelastic is desired to avoid total evacuation of the anterior chamber and collapse of the corneal dome. See also U.S. Pat. No. 5,273,056, which teaches sequential administration of viscoelastics possessing different rheological properties.

Generally, however, all such agents having sufficient viscosity and pseudoplasticity to be useful in ophthalmic surgery will, if left in the eye at the close of surgery, result in a transient increase in intraocular pressure ("IOP") known as an "IOP spike." (See, Obstbaum, *Postoperative pressure elevation. A rational approach to its prevention and management*, J. Cataract Refractive Surgery 18:1 (1992).) The pressure increase has been attributed to the agent's interference with the normal outflow of aqueous humor through the trabecular meshwork and Schlemm's canal. (See, Berson et al., *Obstruction of Aqueous Outflow by Sodium Hyaluronate in Enucleated Human Eyes*, Am. J. Ophthalmology, 95:668 (1983); Olivius et al., *Intraocular pressure after cataract surgery with Healon®*, Am. Intraocular Implant Soc. J. 11:480 (1985); Fry, *Postoperative intraocular pressure rises: A comparison of Healon, Amvis, and Viscoat*, J. Cataract Refractive Surgery 15:415 (1989).) IOP spikes, depending on their magnitude and duration, can cause significant and/or irreversible damage to susceptible ocular tissues, including, without limitation, the optic nerve.

Consequently, viscoelastics are typically removed from the eye just prior to the close of surgery. The ease with which an agent can be removed from the surgical site, typically by aspiration, has traditionally been considered an important characteristic in the overall assessment of the agent's usefulness in cataract surgery. By removing the agent before the close of surgery, the surgeon hopes to minimize or avoid any significant IOP spike. Unfortunately, however, removal of agents which are relatively dispersive (as opposed to cohesive) or which adhere to the ocular tissue is often difficult and may cause additional trauma to the eye.

Alternatives to removing the viscoelastic have been suggested. For example, exogenous dilution of the viscoelastic has been suggested to alleviate IOP spikes. See U.S. Pat. No. 4,328,803. Depending, however, on the particular viscoelastic and the surgical technique employed, IOP spike may still be a problem. More recently, it has been suggested that the administration of degradative agents to break down conventional viscoelastics in the eye can reduce or avoid the occurrence of IOP spikes. See, e.g., U.S. Pat. No. 5,792,103. Such an approach requires not only the administration of an enzymatic agent into the eye, the biocompatability of which must be assured; but also means for adequately mixing the two agents via a special apparatus. Such approaches, which could leave residual material in the eye and thereby result in an IOP spike, have not been adopted by the ophthalmic community, which prefers to aspirate the viscoelastic from the eye at the close of surgery.

There is, therefore, a need for an improved means for reducing or avoiding IOP spikes associated with the use of conventional viscous or viscoelastic agents in ophthalmic surgery, especially cataract surgery. More specifically, the need for an improved methodology that will lend to traditional, hyaluronate-based viscoelastics variable rheological properties that will improve their performance during surgery and facilitate their removal at the end of surgery was recognized. The compositions and methods of the present invention serve this need. More specifically, the present invention involves supplementing the irrigating solution used in such surgeries with relatively low molecular weight polymers that, when mixed with a cohesive hyaluronate-based viscoelastic, have the effect of modifying the rheological properties, and particularly the cohesiveness, of such viscoelastic to improve its performance in surgery.

Irrigating solutions for use in surgery and particularly ophthalmic surgery are well known. See, e.g. commonly assigned U.S. Pat. No. 4,443,432. It has also been suggested that viscous or viscoelastomeric substances may be added to irrigating solutions to reduce cell loss. See commonly assigned U.S. Pat. No. 5,409,904, the contents of which are by this reference incorporated herein. Nothing in such prior art, however, discloses or suggests surface modified viscoelastics or a method of using a modified irrigating solution to effect a reduction in the cohesiveness of a hyaluronate-based viscoelastic in the manner of the present invention.

SUMMARY OF THE INVENTION

The present invention is directed to surface modified viscoelastics and to improved methods of performing surgery, especially ophthalmic surgery, using viscous or viscoelastic agents and an irrigating solution comprising a relatively low molecular weight polymer. More specifically, the inventive methods of the present invention comprise transitioning the rheological properties (specifically viscosity and cohesiveness) of hyaluronate-based viscoelastic agents by exposing such viscoelastic agents to irrigating solutions containing low levels of relatively low molecular weight, biocompatible polymers, such as chondroitin sulfate (CS) and cellulosic polymers, especially hydroxypropylmethylcellulose (HPMC). The hyaluronate-based viscoelastic, at its interface with the polymer-containing irrigating solution, becomes less cohesive and, at the same time, more viscous. The decreased cohesiveness and increased viscosity of the surface hyaluronate interfacing the irrigating solution in situ renders it less susceptible to unintentional aspiration during the surgical procedure. The hyaluronate material that is more distant from such surface (i.e. deeper within the bolus of material) retains its original lower viscosity and higher cohesiveness, and may therefore be readily aspirated at the conclusion of the surgery. In this manner, the skilled surgeon will be able to enjoy the positive aspects of different rheological profiles using the same hyaluronate-based material by modifying its properties at the aforementioned interface with the polymer-containing irrigating solution to suit the particular phase of the surgery, i.e., capsulorhexis, phacoemulsification or aspiration of the viscoelastic.

DETAILED DESCRIPTION OF THE PRESENT INVENTION

While particularly important in ophthalmic surgery, and especially cataract surgery, the compositions and methods of the present invention may be utilized in any viscosurgical procedure, and especially those in which there is concern over unintentional or premature removal of the viscoelastic material from the surgical site. In cataract surgery, the anterior chamber of the eye, i.e. the space between the iris and the corneal endothelium, is filled with viscoelastic. The viscoelastic serves two principal purposes: (1) maintaining the corneal dome to give the surgeon an unobstructed view of the interior surgical site, and (2) protecting the delicate endothelial cells of the cornea by coating them. As discussed above, unsuccessful attempts have been made to find a viscoelastic material with a single, optimized rheology that achieves both of the foregoing objectives. Another approach has been to utilize separate cohesive and dispersive viscoelastic agents in the same surgical procedure. The DuoVisc® product marketed by Alcon Laboratories, Inc. utilizes this latter approach, and has enjoyed commercial success. Nevertheless, it would be preferable if the dual functions of the viscoelastic could be served by a single viscoelastic material. That objective is met using the compositions and methods of the present invention.

We have found that by using an irrigating solution which contains relatively low concentrations of lower molecular weight polymers such as HPMC and CS, the rheology of a cohesive, hyaluronate-based viscoelastic material at the interface of the viscoelastic and the irrigating solution is significantly altered. The viscoelastic at such interface becomes less cohesive and more viscous thereby minimizing inadvertent or premature aspiration and removal of the protective viscoelastic material from the eye. The term "hyaluronate-based viscoelastic" as used herein means any aqueous solution of hyaluronic acid or physiologically acceptable salts thereof, which is free of any significant amount of any low molecular weight polymer. With the exception of Viscoat®, all of the commercial HA products described above are considered hyaluronate-based viscoelastics.

Lens removal surgery, such as cataract surgery or the less common clear lensectomy, involves several different steps or phases. As previously discussed, differing rheological profiles may be preferred for the viscoelastic that is going to be used in each of those steps or phases. For example, during capsulorhexis (opening of the capsular bag to expose the clear or cataractous lens), it is desirable to have a cohesive viscoelastic for space maintenance; during phacoemulsification (ultrasonic fragmentation of the lens) it is desirable to have a dispersive viscoelastic for better coating and maneuverability; finally, during artificial lens insertion and completion of the surgery, it is desirable to have a cohesive viscoelastic both for space maintenance and ease of removal. By using a polymer-containing irrigating solution, as described more fully below, with any of the conventional hyaluronate-based viscoelastic agents, one can, using the methods of the present invention, secure the preferred rheological profile at each step of the procedure.

Preferred methods of the present invention comprise the following steps. A cohesive viscoelastic like PROVISC® (Alcon Laboratories, Inc., Fort Worth, Tex.), HEALON®, or HEALON GV® (Pharmacia & Upjohn, Peapack, N.J.), or AMVISC® PLUS (Bausch & Lomb Surgical, Claremont, Calif.) is used before and during the capsulorhexis step. Then, immediately prior to commencing phacoemulsification, a small amount of polymer-containing irrigating solution is permitted to flow, without aspiration into the space separating the viscoelastic from the anterior surface of the exposed, typically cataractous lens. The phaco emulsification device is then engaged, without irrigation/aspiration, and the tip of the phaco emulsification handpiece is introduced into the surgical site and placed in the irrigating solution above the exposed lens. It is believed that the ultrasonic waves from the tip of the phaco emulsification handpiece will promote the mixture of the irrigating solution and the viscoelastic agent at the interface of those two substances. This will change the cohesive property of the hyaluronate-based viscoelastic in the immediate vicinity of the lens rendering the viscoelastic more dispersive. After up to twenty seconds of mixing, the phacoemulsification of the lens, with irrigation/aspiration, is completed in the ordinary manner. At the end of surgery, the irrigation aspiration tip may be inserted into the bolus of viscoelastic material in the anterior chamber, i.e., beyond the more dispersive surface material at the interface and into the material not affected, or less affected, by admixture with the polymer-containing irrigating solution. The viscoelastic material in this region remains more cohesive and is therefore easily aspirated out with minimal effort and minimal trauma to the delicate endothelial cells.

The cohesive, hyaluronate viscoelastics suitable for use in the methods of the present invention include those commercial products identified above, and may generally be characterized as aqueous solutions containing sodium hyaluronate (of course other physiologically acceptable hyaluronate salts could also be used) having average molecular weights greater than 750,000 Daltons, preferably from about 1,000,000 to about 5,000,000 Daltons, and concentrations from about 0.5 to about 3.0% by weight.

Irrigating solutions that may be used in the methods of the present invention include any sterile, aqueous irrigating solution suitable for surgery. Preferred are balanced salt solutions such as BSS® or BSS® Plus (Alcon Laboratories, Inc., Fort Worth, Tex.). The addition of polymers to the irrigating solution may be effected in the manner described in U.S. Pat. No. 5,409,904, previously incorporated by reference. Virtually any biocompatible, lower molecular weight (i.e. below about 500,000 Daltons) polymer may be used. Examples would include lower molecular weight fractions of the following polymers or combinations thereof: HA, CS, polyacrylamide, HPMC, proteoglycans, collagen, methylcellulose, carboxymethyl cellulose, ethylcellulose, hydroxyethyl cellulose, polyvinylpyrrolidone, keratin, carrageenans, and pharmaceutically acceptable salts thereof, especially sodium salts. Preferred polymeric components for the irrigating solution include CS and HPMC. The preferred, relatively low molecular weight CS suitable for purposes of the present methods would include material having an average molecular weight of less than about 100,000 Daltons, preferably from about 20,000 to about 80,000 Daltons, and most preferably from about 30,000 to about 50,000. Lower molecular weight HPMC used as the polymeric component of the irrigating solution in the present methods will generally have an average molecular weight below about 400,000 Daltons and, preferably from about 50,000 to about 200,000 Daltons, and most preferably from about 70,000 to about 100,000 Daltons. Concentration ranges for the polymeric components will vary depending upon the molecular weight of the polymeric component chosen, but should be maintained at levels low enough to retain the flow properties desired for an irrigating solution. For CS, the concentration in the irrigating solution may be from 0.1 to 10% by weight, preferably from 0.5 to about 7%, and most preferably from about 2% to about 5% by weight. For HPMC, the concentration in the irrigating solution may be from 0.05 to 5% by weight, preferably from about 0.1 to about 0.5%, and most preferably from about 0.2 to about 0.3%. Combinations of different low molecular weight polymers, as exemplified below, may also be used. In a preferred combination, the irrigating solution may contain from about 1.0 to about 3.0% by weight of CS, and from about 0.1 to about 0.3% by weight of HPMC.

The following examples are provided to further illustrate various features of the present invention.

Example 1

A 0.4 mL aliquost of PROVISC or VISCOAT, as the case may be, was placed in a 5 mL reaction vial (conical interior, covered with a flat bottom). To the viscoelastic, 5 microliters of Na fluorescein solution (25% w/v) were added for visualization of the viscoelastic. 0.6 mL of appropriate irrigating solution were then added to the above vial, using a micropipette. The irrigating solution in contact with the viscoelastic was then agitated to promote partial mixing by engaging the ultrasound on the phacoemulsification handpiece tip, and placing such tip in the irrigating solution, (expression of additional irrigating solution should be avoided by lowering the irrigating solution bottle attached to the phacoemulsification unit to a height below the level of the reaction vial). The ultrasound mixing was continued for 20 seconds, while moving the phaco tip, to mix the solution with the viscoelastic, along with the dye. After mixing, the irrigating solution bottle was raised and irrigation/aspiration of the colored viscoelastic mixture was commenced with ultrasound on, working as efficiently as possible. The time taken to fully aspirate the viscoelastic mixture was recorded.

The above steps were repeated twice for each irrigating solution (i.e. a total of 3 runs tested). The results for the various irrigating solutions are as follows:

Aspiration Time (in seconds) for Various Irrigating Solutions/Viscoelastic Combinations

| BSS/PROVISC | BSS/VISCOAT | BSS PLUS PART I + 3.5% CS/PROVISC | BSS + 0.27% HPMC/PROVISC |
|---|---|---|---|
| 10 s | 29 s | 28 s | 31 s |
| 11 s | 30 s | 30 s | 32 s |
| 10 s | 29 s | 27 s | 31 s |
| Average: 10.3 s | 29.3 s | 28.3 s | 31.3 s |

Discussion:

The above results demonstrate that PROVISC®, a cohesive viscoelastic, is aspirated very quickly, when regular BSS is used in the irrigating solution. On the other hand, VISCOAT®, a well known dispersive viscoelastic, takes longer to aspirate. However, when CS or HPMC is in the irrigating solution, aspiration time of PROVISC® is closer to that of VISCOAT®, which indicates in situ changes in the physical properties of the hyaluronate-based viscoelastic.

It should be noted that the irrigating solution was mixed here with the help of ultrasound for 20 seconds, which was likely excessive. In actual surgery the mixing is only required at the interface of the irrigating solution and the viscoelastic, so the actual time needed may be 1 second or less, as the viscosity and cohesiveness of the viscoelastic at the interface changes almost instantly upon mixing.

Example 2

The entire contents of a 0.85 mL syringe containing a 1.0% solution of sodium hyaluronate (marketed as PROVISC® by Alcon) are expressed into a sterile, 5 mL syringe with a tip cap. To the same 5 mL syringe, 0.85 mL of the appropriate irrigating solution (containing low molecular weight polymer) is added to yield a 1:1 ratio. For a 1:2 ratio, 1.7 mL of the irrigating solution is added, and for a 1:3 ratio, 2.55 mL of the irrigating solution is added. The plunger is then carefully inserted into the barrel of the syringe, and the cap on the tip of the syringe is removed. A leur lock connector is affixed on the tip on the syringe, and another (empty) 5 mL syringe is similarly attached on other end of the leur connector. The contents are thoroughly mixed, by alternately pushing plungers of the two conjoined syringes. After repeating this motion a few times, the mixed material is then sonicated for 5 minutes. Finally, the material is centrifuged on a very low setting for 1 min to remove the air bubbles. The contents are then transferred to the plate of a Bohlin Rheometer, through a 27 gauge needle, and the low shear viscosity of the sample is determined in accordance with the manufacturer's instructions.

Using the foregoing procedure, it was confirmed that the low shear viscosity of the viscoelastic (1% sodium hyaluronate) mixed with the polymer-containing irrigating solutions was 3 to 5 times that of the control solution that did not contain the low molecular weight polymeric component.

Example 2A

Generally following the approach described in Example 2, the plunger was removed from a 10 mL sterile plastic syringe, and the cannula end was closed with a tip cap. The syringe was placed upright on a balance with the open end facing up by resting the syringe in a beaker. An appropriate amount of a 1.0% sodium hyaluronate solution (PROVISC®) was transferred into the open syringe and weighed. Then an appropriate amount of the irrigating solution of interest was similarly transferred into the open syringe and weighed. The irrigating solutions were BSS PLUS; BSS PLUS with 0.21% or 0.27% HPMC; and BSS PLUS containing 2% CS. The weight of PROVISC was adjusted such that it was in a 1:1 ratio by weight with the irrigating solution.

After adding the 1.0% sodium hyaluronate material and the irrigating solution to the syringe, the plunger was placed back into the syringe and the tip cap removed. A leur connector was placed on the syringe, where the tip cap had been. Another 10 mL empty sterile syringe was then connected to the other end of the leur connector. The contents of the syringe were thoroughly mixed by alternately pushing plungers of the conjoined syringes for 2 minutes.

After mixing, the contents were sonicated for 30 seconds. After sonication, the contents were further mixed by pushing the plungers a couple of times and the contents were then transferred into a centrifuge tube. The tube was labeled and centrifuged for 2 minutes at low speeds (e.g. 2500 rpm) to remove the air bubbles. The sample was then allowed to sit in a refrigerator overnight. The rheological profile of the product was determined the next day. Preliminary viscosity determination was made without overnight storage of the sample.

The rheological profile was determined by using Bohlin CS Rheometer with a 4° cone and a 40 mm diameter plate (CP 4/40) at a gap width of 0.15 mm. The viscosity was determined at 25° C. Shear stresses between 0.06 and 139 Pa were applied. The corresponding shear rate and viscosity were calculated by the Bohlin software after 200 seconds of integration or whenever the system approved steady state was reached. The results are summarized as follows:

Results

Zero Shear Viscosity of Different Mixtures with 1.0% NaHA (PROVISC)

| Test Material | Zero Shear Viscosity* of 1.0% NaHA and other Solutions mixed in a 1:1 ratio All viscosities are in poise |
| --- | --- |
| 1.0% NaHA | 2240, 2540 |
| 1.0% NaHA + BSS PLUS | 120, 130 |
| 1.0% NaHA + 0.21% HPMC in BSS PLUS | 1530, 1240 |
| 1.0% NaHA + 0.27% HPMC in BSS PLUS | 1800, 1860 |
| 1.0% NaHA + 1.5% CS + 0.12% HPMC in BSS PLUS | 260, 410 |
| 1.0% NaHA + 2.0% CS in BSS PLUS | 230, 210 |

*Zero Shear Viscosity for solutions, was determined by taking average of the viscosities at shear rate of $1 \times 10^{-3}$ to $9.9 \times 10^{-3}$ seconds if a clear plateau was not available. For the solutions having a clear plateau, no averaging was necessary.

As seen from the above table, upon dilution of 1.0% NaHA solution with BSS PLUS in a 1:1 ratio, the viscosity drops exponentially. When CS is present in the solution, the viscosity drop is reduced. In fact, when 2% CS is present in the irrigating solution, viscosity is almost twice that of when CS is not in solution, i.e., two times, that of the control. When HPMC is present in the solution, the reduction of the viscosity drop upon 1:1 dilution is even more dramatic. In fact, viscosity of the resultant solution is almost 10 times that of the control.

Additional Note:

Preliminary viscosity determinations (carried out immediately after the sample preparation rather than the next day) yielded similar results. However, the differences in viscosity enhancement by HPMC was about 3 to 5 times higher, instead of it being 10 times higher when HPMC was present in the irrigating solution. Allowing the samples to sit in a refrigerator overnight seems to help, as the sample settles down and more reproducible viscosity numbers are obtained.

Example 3

| Component | Amount (w/v %) | Function |
| --- | --- | --- |
| HPMC (E4M from Dow Chemical] (Molecular weight: 86,000) | 0.1 to 0.3 | Rheology modifier |
| Sodium Chloride | 0.744 | Tonicity Agent |
| Potassium Chloride | 0.0395 | Essential Ion |
| Dibasic Sodium Phosphate (Anhydrous) | 0.0433 | Buffering Agent |
| Sodium Bicarbonate | 0.219% + 10 to 20% excess | Physiological Buffer |
| Hydrochloric Acid | Adjust Ph | Ph Adjust |
| Sodium Hydroxide | Adjust Ph | Ph Adjust |
| Water for Injection | 100% | Vehicle |

The above-described formulation may be prepared as follows: First, the water for Injection is brought close to boiling or at boiling. The HPMC is then slowly added to the water under continuous stirring to thoroughly disperse it in the water. Then the mixture is slowly allowed to cool, stirring continuously. Once at room temperature, the mixture should start clearing up. Then the mixture is stored overnight at 4° to 8° C. in an appropriate container to fully hydrate the HPMC. The following day, the remaining ingredients are added to the HPMC solution, pH of the solution is adjusted and additional water for injection is added if needed to bring the solution to final volume. The final solution is then filtered, packaged in bottles and autoclaved.

Alternatively, a stock solution of HPMC (1 to 2%) may be prepared first, by an approach similar to that described above. To prepare the stock solution, HPMC is first dispersed in hot water that is close to boiling. Then the mixture is brought to room temperature and chilled to fully hydrate the HPMC. The next day, the stock solution is used as one of the components of the composition. An appropriate amount of stock solution is first added to cooled water for injection. This is followed by the addition of salts, and by pH and volume adjustment.

Example 4

| Component | Amount (w/v %) | Function |
| --- | --- | --- |
| CS (from Seikagaku) (Molecular weight: 40,000) | 2 to 5 | Rheology modifier |
| Sodium Chloride | 0.64 | Tonicity Agent |
| Potassium Chloride | 0.075 | Essential Ion |
| Calcium Chloride (Dihydrate) | 0.048 | Essential Ion |
| Magnesium Chloride (Hexahydrate) | 0.03 | Essential Ion |
| Sodium Acetate (Trihydrate) | 0.039 | Buffering Agent |
| Sodium Citrate (Dihydrate) | 0.17 | Buffering Agent |

-continued

| Component | Amount (w/v %) | Function |
|---|---|---|
| Hydrochloric Acid | Adjust pH | pH Adjust |
| Sodium Hydroxide | Adjust pH | pH Adjust |
| Water for Injection | 100% | Vehicle |

The above-described formulation may be prepared as follows. First, the water for injection is allowed to cool to room temperature. The appropriate quantity of CS is slowly added to the water under continuous stirring to thoroughly disperse it in the water. Stirring continues until all CS is in solution. The remaining ingredients are then added sequentially to the CS solution, making sure that each such ingredient is dissolved before adding the next one. The pH and volume of the solution are then adjusted. The final solution is then sterile filtered and packaged in bottles. The solution may even be terminally sterilized by autoclaving.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of performing ophthalmic surgery comprising:
   during capsulorhexis of a capsular bag, instilling a hyaluronate-based viscoelastic agent into the site of the surgery;
   introducing a polymer-containing irrigating solution into the site of the surgery so that it makes contact with the viscoelastic agent along an interface;
   permitting the irrigating solution to mix with the viscoelastic agent at the interface thereby reducing the cohesiveness of the viscoelastic agent along the interface; and
   removing said viscoelastic before closing the capsular bag.

2. The method of claim 1, wherein the hyaluronate-based viscoelastic is an aqueous solution of sodium hyaluronate having an average molecular weight greater than 750,000 Daltons and a concentration of from about 0.5% to about 3% by weight.

3. The method of claim 1, wherein the polymer-containing irrigating solution contains a polymer having an average molecular weight of less than 500,000 Daltons, which polymer is selected from the group consisting of: HA, CS, polyacrylamide, HPMC, proteoglycans, collagen, methylcellulose, carboxymethyl cellulose, ethylcellulose, hydroxyethyl cellulose, polyvinylpyrrolidone, keratin, carrageenans, and pharmaceutically acceptable salts and combinations thereof.

4. The method of claim 3, wherein the polymer-containing irrigating solution contains chondroitin sulfate at a concentration of from about 0.5% to about 7% by weight.

5. The method of claim 4, wherein the concentration of the chondroitin sulfate in the irrigating solution is from about 2% to about 5% by weight and the chondroitin sulfate has an average molecular weight of from about 20,000 to about 80,000 Daltons.

6. The method of claim 3, wherein the polymer-containing irrigating solution contains hydroxypropylmethyl cellulose at a concentration of from about 0.05% to about 5.0% by weight.

7. The method of claim 4, wherein the concentration of the hydroxypropylmethyl cellulose in the irrigating solution is from about 0.1% to about 0.5% by weight and has an average molecular weight of from about 50,000 to about 200,000 Daltons.

8. The method of claim 1, wherein said permitting the irrigating solution to mix with the viscoelastic agent at the interface comprises mixing using ultrasonic waves.

9. The method of claim 8 wherein said mixing takes place during phacoemulsification.

10. The method of claim 3 wherein the polymer-containing irrigating solution contains hydroxypropylmethyl cellulose at a concentration of from about 0.05% to about 5.0% by weight and chondroitin sulfate at a concentration of from about 0.5% to about 7% by weight.

* * * * *